US010987424B2

(12) United States Patent
Lim et al.

(10) Patent No.: US 10,987,424 B2
(45) Date of Patent: Apr. 27, 2021

(54) LIQUID FORMULATION OF LONG-ACTING INSULIN CONJUGATE

(71) Applicant: HANMI PHARM. CO., LTD., Hwaseong-si (KR)

(72) Inventors: Hyung Kyu Lim, Hwaseong-si (KR); Hyun Uk Kim, Busan (KR); Sung Hee Hong, Suwon-si (KR); Min Young Kim, Suwon-si (KR); Sung Min Bae, Seongnam-si (KR); Se Chang Kwon, Seoul (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 14/415,206

(22) PCT Filed: Jul. 25, 2013

(86) PCT No.: PCT/KR2013/006673
§ 371 (c)(1),
(2) Date: Jan. 16, 2015

(87) PCT Pub. No.: WO2014/017847
PCT Pub. Date: Jan. 30, 2014

(65) Prior Publication Data
US 2015/0196643 A1    Jul. 16, 2015

(30) Foreign Application Priority Data

Jul. 25, 2012 (KR) .................. 10-2012-0081477

(51) Int. Cl.
| A61K 47/68 | (2017.01) |
| A61K 47/26 | (2006.01) |
| A61K 38/28 | (2006.01) |
| A61K 47/02 | (2006.01) |
| A61K 47/10 | (2017.01) |
| A61K 47/12 | (2006.01) |

(52) U.S. Cl.
CPC .............. *A61K 47/26* (2013.01); *A61K 38/28* (2013.01); *A61K 47/02* (2013.01); *A61K 47/10* (2013.01); *A61K 47/12* (2013.01); *A61K 47/68* (2017.08)

(58) Field of Classification Search
None
See application file for complete search history.

(56) References Cited

U.S. PATENT DOCUMENTS

| 5,783,556 A * | 7/1998 | Clark .................. A61K 9/0019 |
| | | 514/6.4 |
| 6,756,480 B2 | 6/2004 | Kostenuik et al. |
| 6,924,264 B1 | 8/2005 | Prickett et al. |
| 2002/0019352 A1 | 2/2002 | Brems et al. |
| 2003/0054979 A1 * | 3/2003 | Kim .................. A61K 9/0019 |
| | | 514/6.5 |
| 2006/0183197 A1 | 8/2006 | Andersen et al. |
| 2010/0196405 A1 | 8/2010 | Ng |
| 2010/0330108 A1 | 12/2010 | Song et al. |

FOREIGN PATENT DOCUMENTS

| CN | 101730523 A | 6/2010 |
| CN | 101878036 A | 11/2010 |
| EP | 0 413 622 B1 | 2/1998 |
| JP | 2008-150369 A | 7/2008 |
| JP | 2010-533197 A | 10/2010 |
| JP | 6385925 B2 | 9/2018 |
| KR | 10-0567902 B1 | 4/2006 |
| KR | 10-0725315 B1 | 6/2007 |
| KR | 10-2011-0111267 A | 10/2011 |
| KR | 10-2011-0134209 A | 12/2011 |
| KR | 10-2011-0134210 A | 12/2011 |
| RU | 2 248 214 | 11/2003 |
| RU | 2 358 763 | 6/2006 |
| RU | 2 354 366 | 9/2006 |
| WO | 93/15199 A1 | 8/1993 |
| WO | 93/15200 A1 | 8/1993 |
| WO | 96/32478 A1 | 10/1996 |
| WO | 97/34631 A1 | 9/1997 |
| WO | 02/46227 A2 | 6/2002 |
| WO | 2006/076471 A2 | 7/2006 |
| WO | 2009/009562 A2 | 1/2009 |
| WO | 2009/069983 A2 | 6/2009 |
| WO | 2011/041003 | 4/2011 |
| WO | 2011/090306 A2 | 7/2011 |
| WO | 2011/122921 A2 | 10/2011 |
| WO | 2012/008779 A2 | 1/2012 |
| WO | 2012/057525 A2 | 5/2012 |

OTHER PUBLICATIONS

Kling, Highly Concentrated Protein Formulations:Finding Solutions for the Next Generation of Parenteral Biologics (2014), pp. 1-17 of 17.*
International Searching Authority, International Search Report of PCT/KR2013/006673 dated Nov. 14, 2013.
International Searching Authority, Written Opinion of the International Searching Authority of PCT/KR2013/006673 dated Nov. 14, 2013.

(Continued)

*Primary Examiner* — Jessica Worsham
(74) *Attorney, Agent, or Firm* — Sughrue Mion, PLLC

(57) ABSTRACT

The present invention relates to a liquid formulation of long-acting insulin conjugate, comprising a pharmaceutically effective amount of a long-acting insulin conjugate, wherein a physiologically active peptide, which is an insulin, is linked to an immunoglobulin Fc region; and an albumin-free stabilizer, wherein the stabilizer comprises a buffer, a sugar alcohol, a non-ionic surfactant, and an isotonic agent, and a method for preparing the formulation. For preventing microbial contamination in multiple uses, a preservative can be added to the formulation. The liquid formulation of the present invention does not comprise a human serum albumin and potentially hazardous factors to body, and thus it has excellent storage stability for insulin conjugate without a risk of viral infection.

26 Claims, 2 Drawing Sheets
Specification includes a Sequence Listing.

(56) References Cited

OTHER PUBLICATIONS

European Patent Office, Communication dated May 3, 2016 issued in corresponding Application No. 13822348.2.
State Intellectual Property Office of the P.R.C.; Communication dated Jun. 14, 2016 in counterpart CN application No. 201380039653.4.
Japanese Patent Office, Communication dated Apr. 3, 2017, issued in counterpart Japanese Application No. 2015-524184.
Russian Patent Office, Communication dated Jul. 20, 2017 by the Russian Patent Office in counterpart Russian Application No. 2015104495/15(007050).

* cited by examiner

※¹ #1 (0.2%(V/V) polysorbate 20)
: protein precipitation after 3 weeks
※² #3 (20mg/mL NaCl 0.2%(V/V) polysorbate 20)
: protein precipitation after 1 weeks

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

```
<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

LIQUID FORMULATION OF LONG-ACTING INSULIN CONJUGATE

CROSS REFERENCE TO RELATED APPLICATIONS

This is a National Stage of International Application No. PCT/KR2013/006673 filed Jul. 25, 2013, claiming priority based on Korean Patent Application No. 10-2012-0081477 filed Jul. 25, 2012, the contents of all of which are incorporated herein by reference in their entirety.

TECHNICAL FIELD

The present invention relates to a liquid formulation of long-acting insulin conjugate, comprising a pharmaceutically effective amount of a long-acting insulin conjugate, wherein an insulin which is a physiologically active peptide is linked to an immunoglobulin Fc region; and an albumin-free stabilizer, wherein the stabilizer comprises a buffer, a sugar alcohol, a non-ionic surfactant, and an isotonic agent, and a method for preparing the formulation.

BACKGROUND ART

Insulin is a peptide consisting of 51 amino acids having a molecular weight of about 5,800 Da. Insulin is secreted by the human pancreatic beta cells, and plays a central role in the control of blood glucose levels in the body. If the amount of insulin secreted is lacking or the secreted insulin does not function properly in the body, the blood glucose level will be elevated, causing metabolic disease called diabetes. When the insulin is not secreted properly or does not function properly in the body, the blood glucose level cannot be regulated, and this type of diabetes is called type II diabetes. Type I diabetes is caused when the pancreas does not make enough insulin to regulate the increase of blood glucose level. Type II diabetes is usually treated with oral hypoglycemic agents mainly consisting of chemical compounds, and in some cases, the patients are treated by using insulin. Meanwhile, type I diabetes requires administration of insulin.

The currently used insulin treatment is an injection of insulin before and after meals. However, such insulin injection should be done three times a day continuously, which causes severe pain or discomfort to the patients. There have been many attempts to solve these problems, and one of them was the delivering of a peptide drug into the body through oral or nasal inhalation by increasing the biomembrane permeability of the peptide drug. However, this method has significantly low efficiency for delivering the peptide into the body compared to injections. Therefore, there are still many limitations in maintaining the activity of peptide drug in vivo at the required level.

Meanwhile, another method for delivering drug was by delaying a drug absorption after a subcutaneous injection of a large amount of drug, so as to maintain a continuous drug level in blood by doing only a single injection a day. Some of the drugs (e.g. Lantus? Sanofi-aventis) were approved as a drug, and are currently being administered to the patients. In addition, studies have been conducted to extend the in vivo durability through making the bond in insulin conjugate stronger by modifying insulin with fatty acid, and through making the insulin to bind with albumin in administration site and blood, which led to the development of Levemir (NovoNordisk) which is approved as drug. However, these methods have a side effect of causing pain at the site of injection, and the daily injections are still undue burden to the patient.

Meanwhile, there have been continuous attempts to maximize therapeutic effects of a peptide drug by improving the stability thereof in blood and maintaining a high drug level in blood for a long period of time after absorption of the peptide drug into the body. The long-acting formulation of the peptide drugs should promote an increased stability of peptide drug and also maintain a sufficiently high titer of drug itself without inducing immune responses in patients. For the preparation of the long-acting formulations of peptide drugs, a polymer having high solubility, such as polyethylene glycol (PEG), has been used to chemically modify the surface of a peptide drug.

PEG binds to a specific site or various sites of a target peptide non-specifically and increases the molecular weight of the peptide, which then prevents the loss of peptide in kidney and hydrolysis of peptide, without causing side effects. For example, International Patent Publication WO2006/076471 discloses that by attaching PEG to a B-type natriuretic peptide (BNP), which activates production of cGMP by binding to NPR-A and reduces intra-arterial blood pressure, thereby being effective as therapeutic agent for congestive heart failure, the bioactivity of BNP can be maintained. Likewise, U.S. Pat. No. 6,924,264 describes a method for increasing the in vivo durability of exendin-4 by attaching PEG to lysine residue of an exendin-4. However, while these methods can extend the in vivo durability of a peptide drug by increasing the PEG molecular weight, the titer of the peptide drug gets reduced as the PEG molecular weight increases.

As another method for increasing the in vivo stability of physiologically active proteins, a method for preparing a fusion protein has been developed. In this method, the gene for protein having high serum stability and the gene for a physiologically active protein are linked by genetic recombination, and the animal cells transformed with the recombinant gene are cultured to produce a fusion protein. For example, it has been reported that a fusion protein can be prepared by linking an albumin or fragments thereof, which are highly effective in increasing protein stability, to a desired physiologically active protein through genetic recombination (International Patent Publication Nos. WO 93/15199 and WO 93/15200, and European Patent Publication No. EP 413,622).

International Patent Publication No. WO 02/46227 describes a fusion protein prepared by coupling GLP-1, exendin-4, or analog thereof with a human serum albumin or an immunoglobulin fragment (Fc) through genetic recombination. U.S. Pat. No. 6,756,480 describes a fusion protein prepared by coupling a parathyroid hormone (PTH) or an analog thereof with an immunoglobulin fragment (Fc). These methods may overcome the problems of low pegylation yield and non-specificity, but they still have a limitation in that it cannot increase the half-life of peptide in blood significantly, and in some cases, the titers are low. In order to maximize the effect of increasing the blood half-life, various types of peptide linkers have been used, but there is a possibility of causing an immune response. Furthermore, if a peptide having disulfide bonds, such as BNP, is used, there is a high possibility of misfolding, and if there is unnatural amino acid residue in a peptide linker, it cannot be produced by genetic recombination.

Recently, as a long-acting protein drug formulation which can promote a minimal reduction in activity and an increased stability, a conjugate generated by combining an immunoglobulin Fc region, a non-peptidyl polymer, and a physiologically active polypeptide is disclosed in Korean Patent Registration No. 10-0567902 (Physiologically active polypeptide conjugate having improved in vivo durability) and Korean Patent Registration No. 10-0725315 (Protein complex using an immunoglobulin fragment and method for the preparation thereof).

Furthermore, Korean Patent Publication No. 10-2011-0134210 (Insulin derivative drug conjugate using immunoglobulin fragment) discloses that an insulin conjugate generated by linking an immunoglobulin Fc region, a non-peptidyl polymer, and a PEG-modified insulin analog site-specifically through covalent bond showed an improved half-life in blood and reduced the risk of having a low blood glucose level in the body. Through the above method, insulin may be applied as a physiologically active polypeptide for preparing a long-acting insulin conjugate. To manufacture the drug comprising long-acting insulin conjugate, it is essential to prevent physiochemical changes such as heat-induced denaturation, aggregation, adsorption, or hydrolysis caused by light, heat, or impurities in additives during storage and delivery processes while maintaining in vivo efficacy. The long-acting insulin conjugate has larger volume and molecular weight compared to the insulin peptide itself, and thus it is hard to stabilize.

Due to their chemical differences, different proteins may be gradually inactivated at different rates under different conditions during storage. That is, the extension of storage term by a stabilizer is not the same for different proteins. For this reason, the suitable ratio, concentration, and type of stabilizers that are used to improve storage stability of proteins vary depending on the physiochemical properties of a target protein. Furthermore, when different stabilizers are used together, they may induce adverse effects different from those desired, due to competitive interaction and side effects. Also, during storage, the property of stored protein or concentration thereof can change, thereby causing different effects. Therefore, a lot of efforts and cautions are needed to stabilize a protein in solution. In particular, as for the long-acting insulin conjugate having improved in vivo durability and stability, it consists of a physiologically active peptide, insulin, linked with an immunoglobulin Fc region, and thus the molecular weight and volume thereof are significantly different from general insulin, thereby requiring a specific composition for stabilizing protein.

Also, a physiologically active peptide, insulin and an immunoglobulin Fc region are physiochemically different peptide or protein, and thus they have to be stabilized concurrently. However, as described above, different peptides or proteins may be gradually inactivated at different rates under different conditions during storage due to the physiochemical difference thereof. Also, when the stabilizers that are suitable for each of peptide or protein are used together, they may induce adverse effects different from desired effects, due to competitive interaction and side effects. Therefore, as for a long-acting insulin conjugate, it is highly difficult to find a stabilizer composition that can stabilize both a physiologically active peptide, insulin, and an immunoglobulin Fc region concurrently.

Recently, a formulation of protein and peptide that can be used repeatedly for the patient's convenience has been developed. However, the multiple-use formulation must contain a preservative to prevent the microbial contamination after repeated administrations and prior to disposal. The multiple-use formulation containing preservative has a few advantages compared to a single-use formulation. For example, as for a single-use formulation, a large amount of drug is wasted depending on the difference in dosage. But by using a multiple-use formulation, the amount of product wasted can be reduced. Furthermore, the multiple-use formulation can be used several times without concerning about microbial growth within certain period, and since it can be supplied in a single container, packing can be minimized, leading to economic benefits. However, use of preservative may affect the protein stability. The most well-known problem in use of preservative is precipitation issue. Precipitation of protein can reduce therapeutic effects of drug and when administered to the body it can induce unexpected immune response. Therefore, it is critical to select an appropriate concentration and type of preservative that maintain the ability to prevent microbial contamination while not affecting protein stability.

DISCLOSURE

Technical Problem

Given this background, in an effort to provide a stable liquid formulation of long-acting insulin conjugate which can be stored for a long period of time without a risk of viral contamination to the long-acting insulin conjugate, the present inventors have developed a liquid formulation that can improve the stability of long-acting insulin conjugate by using a stabilizer comprising a buffer, a sugar alcohol, a non-ionic surfactant, and an isotonic agent and that can be used multiple times if a preservative is added, and further confirmed that a cost-effective and stable liquid formulation can be prepared, thereby completing the present invention.

Technical Solution

One object of the present invention is to provide a liquid formulation of long-acting insulin conjugate, comprising a pharmaceutically effective amount of a long-acting insulin conjugate, wherein an insulin which is a physiologically active peptide is linked to an immunoglobulin Fc region; and an albumin-free stabilizer, wherein the stabilizer comprises a buffer, a sugar alcohol, a non-ionic surfactant, and an isotonic agent.

Another object of the present invention is to provide a liquid formulation of long-acting insulin conjugate for multiple administrations, which comprises a preservative in addition to the long-acting insulin conjugate and albumin-free stabilizer.

Another object of the present invention is to provide a method for preparing the liquid formulation.

Another object of the present invention is to provide a pharmaceutical composition for preventing or treating diabetes, comprising a long-acting insulin conjugate, wherein an insulin which is a physiologically active peptide is linked to an immunoglobulin Fc region.

Another object of the present invention is to provide a method for treating diabetes, comprising administering the composition to a subject having diabetes.

Advantageous Effects

As the liquid formulation of long-acting insulin conjugate of the present invention comprises a stabilizer comprising a buffer, a sugar alcohol, an isotonic agent, and a non-ionic surfactant, but is free of human serum albumin and other potentially hazardous factors to body, and therefore there is no risk of viral contamination. Also, it can provide excellent storage stability for a long-acting insulin conjugate which consists of an insulin and an immunoglobulin Fc region, thereby having higher molecular weight and enhanced in vivo duration of physiological activity compared to the wild-type protein. In addition, if a preservative is added to the formulation, the liquid formulation can be stably used multiple times. In particular, the present invention provides excellent and stable liquid formulation for the long-acting insulin conjugate. Such liquid formulation of the present invention can provide excellent storage stability with simple formulation and provide the peptide drug more cost-effectively compared to other stabilizer and freeze-drier. Also, the present formulation can retain the protein activity in the body for a longer period compared to a conventional insulin formulation, and thus it can be used as an effective drug formulation.

BEST MODE

Figure 1:
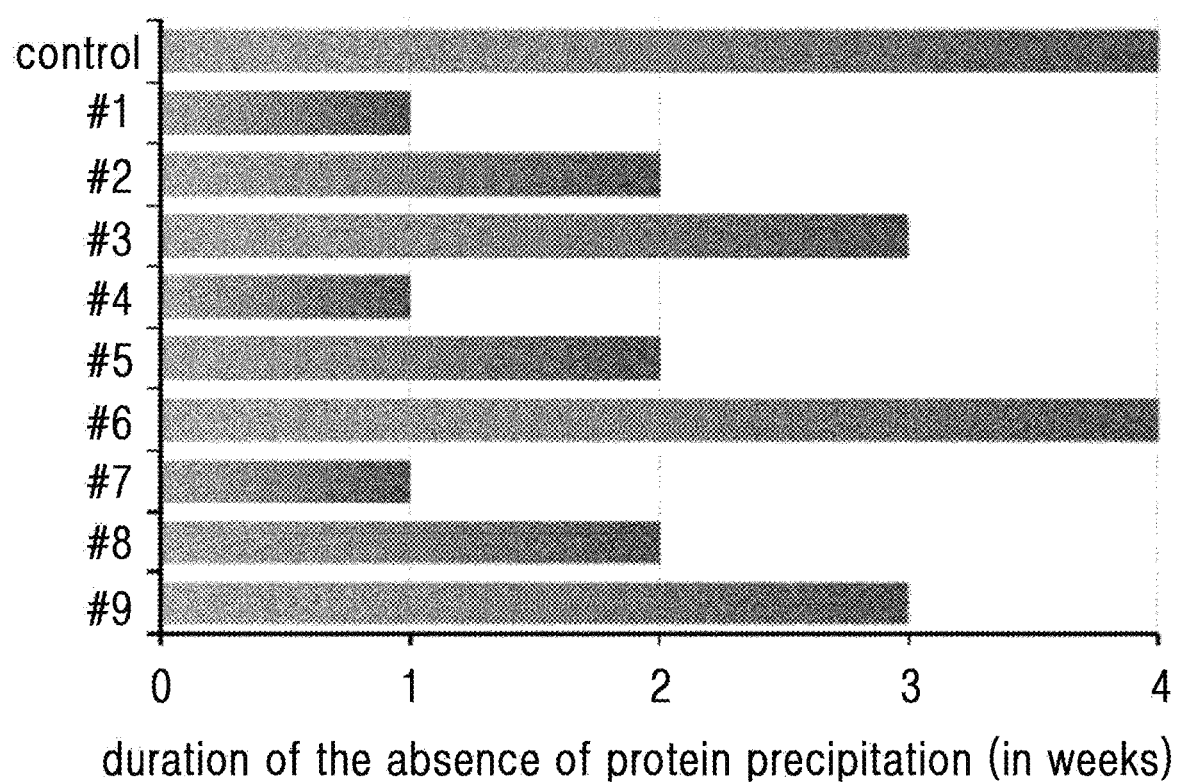
FIG. 1 shows the duration of the absence of precipitation of long-acting insulin conjugates in the compositions of Table 7 as monitored at 40° C. for 4 weeks with naked eyes. The duration of the absence of precipitation indicates the time during which a protein precipitation did not occur after storing the conjugate.

As one aspect to achieve the object, the present invention provides a liquid formulation of long-acting insulin conjugate, comprising a pharmaceutically effective amount of a long-acting insulin conjugate, wherein an insulin which is a physiologically active peptide is linked to an immunoglobulin Fc region; and an albumin-free stabilizer, wherein the stabilizer comprises a buffer, a sugar alcohol, a non-ionic surfactant, and an isotonic agent. Also, the present invention provides a formulation that can be used multiple times if the formulation comprises preservative.

Also, the present invention provides a liquid formulation of long-acting insulin conjugate for multiple administrations, which comprises a preservative in addition to the long-acting insulin conjugate and albumin-free stabilizer.

As used herein, "long-acting insulin conjugate"? refers to a conjugate wherein a physiologically active insulin comprising derivative, variant, precursor, and fragment and an immunoglobulin Fc region are linked, and it may refer to a conjugate having increased in vivo duration of physiological activity compared to a wild-type insulin. As used herein, long-acting insulin conjugate refers to the insulin linked with an immunoglobulin Fc region through non-peptidyl linker or peptidyl linker.

As used herein, the term "long-acting" refers to an enhancement of duration of physiological activity compared to that of a wild-type. The term "conjugate" refers to the form wherein an insulin and immunoglobulin Fc region are combined.

The long-acting insulin conjugate has an enhanced duration of activity compared to native insulin. The type of the long-acting insulin conjugate includes a form of insulin prepared by modification, substitution, addition, or deletion of amino acids of native insulin, a conjugate where insulin is linked with a biodegradable polymer such as PEG, a conjugate where insulin is linked with a protein with high durability such as albumin and immunoglobulin, a conjugate where insulin is linked with a fatty acid which has a binding affinity with albumin in the body, or a form of insulin where insulin is filled in a biodegradable nano-particle, but is not limited thereto.

The long-acting insulin conjugate used in the present invention is prepared by combining the synthesized insulin and an immunoglobulin Fc region. The method for combining the two may be cross-linking insulin and an immunoglobulin Fc region via a non-peptidyl polymer or the production of a fusion protein in which insulin and an immunoglobulin Fc region are linked by genetic recombination.

As used herein, "insulin" refers to a peptide that is secreted by pancreas in response to elevated glucose levels in the blood to take up glucose in the liver, muscle, or adipose tissue and turn it into glycogen, and to stop the use of fat as an energy source, and thus functions to control the blood glucose level. This peptide includes native insulin, basal insulin, and the agonists, precursors, derivatives, fragments, and variants thereof.

As used herein, "native insulin" is a hormone that is secreted by pancreas to promote glucose absorption and inhibit fat breakdown, and thus functions to control the blood glucose level. Insulin is generated from processing its precursor, proinsulin, which does not have a function of regulating blood glucose level. The amino acid sequences of insulin are as follows:

```
Alpha chain:
                                        (SEQ ID NO. 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta chain:
                                        (SEQ ID NO. 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

As used herein, "basal insulin" refers to a peptide regulating normal blood glucose level changes during each day, and examples of such peptide include levemir, glagine, and deglude. As used herein, "insulin agonist" refers to a compound that binds to the intrinsic receptor of insulin showing the same biological activity as insulin, regardless of the structural difference with insulin. As used herein, "insulin variant" refers to a peptide having one or more different amino acid sequence from the native insulin, which has a function of regulating the blood glucose level in the body. The insulin derivative may be prepared by one of substitution, addition, deletion, and modification of some amino acids of native insulin or a combination thereof. As used herein, "insulin derivative" refers to a peptide having at least 80% amino acid sequence homology with the native insulin, which may have some groups on the amino acid residue chemically substituted (e.g., alpha-methylation, alpha-hydroxylation), deleted (e.g., deamination), or modified (e.g., N-methylation), and has a function of regulating the blood glucose level in the body. As used herein, "insulin fragment" refers to a fragment having one or more amino acids added or deleted at the N-terminal or the C-terminal of the native insulin, in which non-naturally occurring amino acids (e.g., D-type amino acid) can be added. The insulin fragment has a function of regulating the blood glucose level in the body.

Each of the preparation methods for the agonists, derivatives, fragments, and variants of insulin can be applied individually or concurrently. For example, the scope of the present invention comprises a peptide that has one or more amino acid sequences different from those of native peptide and the N-terminal amino acid residue deaminated, while having a function of regulating the blood glucose level in the body. The insulin used in the present invention may be produced by a recombination technology or synthesized by a solid phase synthesis. Also, the insulin used in the present invention may be linked with a non-peptidyl polymer at the N-terminal of beta-chain thereof. Such non-peptidyl polymer can be used as a linker in the present invention. By combining the insulin with the non-peptidyl polymer as a linker, the stability of insulin can be improved while maintaining its activity.

As used herein, "non-peptidyl polymer" refers to a biocompatible polymer combined with one or more repeating units, wherein the repeating units are linked to each other through any covalent bond, but not by a peptide bond. In the present invention, the "non-peptidyl polymer"?can be used interchangeably with "non-peptidyl linker".

The non-peptidyl polymer which can be used in the present invention may be selected from the group consisting of biodegradable polymers such as polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid (PLA), and polylactic-glycolic acid (PLGA); lipid polymers, chitins, hyaluronic acid, and a combination thereof. Preferably, polyethylene glycol is used as the non-peptidyl polymer, but is not limited thereto. The scope of the present invention also includes the derivatives thereof that are well-known in the art and that can be easily prepared using the techniques available in the art.

The peptidyl linker used in a fusion protein, which is prepared by a conventional inframe fusion method, has a limitation in that it can be easily cleaved by protease in the body, and thus it cannot increase the serum half-life of active drug sufficiently as much as when a carrier is used. However, if a polymer resistant to the protease is used, the serum half-life of the peptide can be maintained as similar to when a carrier is used. Therefore, any non-peptidyl polymer can be used without limitation, as long as it has the aforementioned function, that is, being resistant to protease. The non-peptidyl polymer has a molecular weight of 1 to 100 kDa, and preferably 1 to 20 kDa. Also, the non-peptidyl polymer of the present invention, which is linked to an immunoglobulin Fc region, may be a single type of polymers or a combination of different types of polymers.

The non-peptidyl polymer may have a function group that can be bound to the immunoglobulin Fc region and protein drug. The functional groups of the non-peptidyl polymer at both terminals are preferably selected from the group consisting of a reactive aldehyde group, a propionaldehyde group, a butyl aldehyde group, a maleimide group, and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both terminals, this can minimize the non-specific bindings and can make effective linking of the non-peptidyl polymer with a physiologically active polypeptide and an immunoglobulin at each of the terminals. A final product generated by reductive alkylation by an aldehyde bond is much more stable than those linked by an amide bond. An aldehyde functional group selectively binds to the N-terminal at low pH, and forms a covalent bond with a lysine residue at high pH, for example at a pH of 9.0. The functional groups at two terminals of the non-peptidyl polymer may be the same or different. For example, the non-peptide polymer may have a maleimide group at one terminal, and an aldehyde group, a propionaldehyde group or a butyl aldehyde group at the other terminal. When a polyethylene glycol having a hydroxy group at both terminals is used as a non-peptidyl polymer, the hydroxy group may be activated into various functional groups by known chemical reactions, or a commercially available polyethylene glycol having modified functional group may be used so as to prepare the long-acting insulin conjugate of the present invention.

Preferably, the non-peptidyl polymer may be linked to the N-terminal of beta-chain of insulin.

The insulin of the present invention may be reformed with a non-peptidyl polymer. When developing a long-acting insulin conjugate by using immunoglobulin fragment, if a physiologically active polypeptide is modified with PEG for increasing the durability of drug while avoiding low blood glucose level, this may reduce titer, however this acts as an advantage in the long-acting insulin conjugate. Therefore, the insulin modified with PEG can be combined with immunoglobulin Fc region through non-peptidyl polymer. The type of non-peptidyl polymer that can be used in reforming insulin is the same as described above, and preferably polyethylene glycol (PEG). In the PEG-modified insulin, the PEG is selectively linked to the N-terminal of alpha-chain of insulin or to a specific lysine residue of beta-chain. PEG that modifies the insulin preferably comprises aldehyde group or succinyl group at the terminal, and more preferably succinyl group.

The preparation method and effect of the long-acting insulin conjugate of the present invention are disclosed in Korean Patent Publication Nos. 10-2011-0134210, 10-2011-0134209, and 10-2011-0111267. Those skilled in the art can prepare the long-acting insulin conjugate used in the present invention by referring to these references. Also, the present inventors have previously provided a method for preparing the long-acting insulin conjugate by mono-PEGylation of the N-terminal of immunoglobulin Fc region, and modifying the same to the $1^{st}$ phenylalanine of beta-chain of insulin.

The insulin used in the present invention is linked with a carrier through a non-peptidyl polymer as a linker. The carrier that can be used in the present invention can be selected from the group consisting of immunoglobulin Fc region, albumin, transferrin, and PEG, and is preferably immunoglobulin Fc region.

The long-acting insulin conjugate of the present invention has insulin linked to immunoglobulin Fc region through non-peptidyl linker, having durability and stability. In the present invention, the immunoglobulin Fc can be interchangeably used with immunoglobulin fragment.

In addition, since immunoglobulin Fc region has a relatively low molecular weight compared to the whole immunoglobulin molecule, a use thereof can be beneficial for preparing and purifying the conjugate as well as for getting high yield. Furthermore, the immunoglobulin Fc region does not contain a Fab fragment, which is highly non-homogenous due to different amino acid sequences according to the antibody subclasses, and thus it can be expected that the immunoglobulin Fc region has an increased homogeneity and is less antigenic.

As used herein, "immunoglobulin Fc region"? refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, it may be a fragment having a deletion in a relatively long portion of the amino acid sequence of CH2 and/or CH3. That is, the immunoglobulin Fc region of the present invention may comprise (1) a CH1 domain, a CH2 domain, a CH3 domain and a CH4 domain, (2) a CH1 domain and a CH2 domain, (3) a CH1 domain and a CH3 domain, (4) a CH2 domain and a CH3 domain, (5) a combination of one or more domains and an immunoglobulin hinge region (or a portion of the hinge region), and (6) a dimer of each domain of the heavy-chain constant regions and the light-chain constant region.

Further, the immunoglobulin Fc region of the present invention includes a native amino acid sequence and a sequence derivative (mutant) thereof. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

In addition, other various derivatives are possible, including derivatives having a deletion of a region capable of forming a disulfide bond, a deletion of several amino acid residues at the N-terminus of a native Fc form, or an addition of methionine residue to the N-terminus of a native Fc form. Furthermore, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions. The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to that of the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$ fragments. These fragments may be subjected, for example, to size-exclusion chromatography to isolate Fc or pF'c. Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation" as used herein, means to enzymatically remove sugar moieties from an Fc region, and the term "aglycosylation"? means that an Fc region is produced in an unglycosylated form by a prokaryote, preferably *E. coli*.

Meanwhile, the immunoglobulin Fc region may be derived from human or animals such as cows, goats, pigs, mouse, rabbits, hamsters, rats, guinea pigs, and preferably human.

In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in the human blood, and most preferably from IgG, which is known to enhance the half-life of ligand-binding proteins.

The term "combination" as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid" as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations or hybrids thereof. Preferred are IgG2 and IgG4 subclasses, and most preferred is the Fc region of IgG4 rarely having effector functions such as complement dependent cytotoxicity (CDC).

As the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The liquid formulation of long-acting insulin conjugate of the present invention comprises a therapeutically effective amount of long-acting insulin conjugate. The concentration of long-acting insulin conjugate used in the present invention is 0.1 mg/ml to 200 mg/ml, and preferably 10 mg/ml to 200 mg/ml. The liquid formulation of long-acting insulin conjugate of the present invention can stably store the conjugate without precipitation not only when the insulin conjugate is present at low concentration, but also when it is at high concentration, and thus it can stably provide the insulin at high concentration into the body.

As used herein, the term "stabilizer" refers to a substance that allows stable storing of the long-acting insulin conjugate. The term "stabilization" refers to that the loss of an active ingredient is less than a certain amount, typically less than 10% during certain period and under specific storage condition. A formulation is regarded as stable formulation when the residual purity of long-acting insulin conjugate therein is 90% or more, and more preferably 92 to 95% after being stored at 5±3° C. for 2 years, at 25±2° C. for 6 months, or at 40±2° C. for 1 to 2 weeks. As for the proteins like long-acting insulin conjugates, the storage stability thereof is important for providing an accurate dosage as well as for suppressing the potential formation of antigenic substances against the long-acting insulin conjugate. During storage, 10% loss of long-acting insulin conjugate is acceptable for a substantial administration unless it causes the formation of aggregates or fragments in the composition leading to the formation of antigenic compounds.

The stabilizer of the present invention preferably comprises a buffer, a sugar alcohol, a sodium chloride as isotonic agent, and a non-ionic surfactant for stabilizing the long-acting insulin conjugate.

The buffer works to maintain the pH of solution to prevent a sharp pH change in the liquid formulation for stabilizing long-acting insulin conjugate. The buffer may include an alkaline salt (sodium or potassium phosphate or hydrogen or dihydrogen salts thereof), sodium citrate/citric acid, sodium acetate/acetic acid, and any other pharmaceutically acceptable pH buffer known in the art, and a combination thereof. The preferred example of such buffer is a sodium acetate buffer (Na-Acetate buffer). The concentration of acetic acid constituting a sodium acetate buffer is preferably 5 mM to 100 mM, more preferably 5 mM to 50 mM. The pH of buffer is preferably 4.0 to 8.0, more preferably 4.0 to 7.0, and even more preferably 5.0 to 7.0.

Sugar alcohol acts to increase the stability of the long-acting insulin conjugate. In the present invention, sugar alcohol is used preferably in an amount of from 1 to 20% (w/v) and more preferably in an amount of 2 to 15% (w/v) based on the total volume of the formulation. Examples of the sugar alcohol useful in the present invention include mannitol, sorbitol but preferably mannitol.

Isotonic agent has the effect of maintaining the proper osmotic pressure when a solution of the insulin conjugate is being injected into the body as well as further stabilizing the long-acting insulin conjugate in solution. Isotonic agent is typically a water-soluble inorganic salt, including sodium chloride, sodium sulfate, sodium citrate and preferably sodium chloride. The content of isotonic agent may be adjusted appropriately according to the type and amount of components included in the formulation so that a liquid formulation comprising all the mixture can be an isotonic solution. For example, the isotonic agent may be used at a concentration of 1 mg/ml to 20 mg/ml.

The non-ionic surfactant reduces the surface tension of the protein solution to prevent the absorption or aggregation of proteins onto a hydrophobic surface. Examples of the non-ionic surfactant useful in the present invention include polysorbates, poloxamers and combinations thereof, with preference for polysorbates. Among the non-ionic surfactants of polysorbates are polysorbate 20, polysorbate 40, polysorbate 60, and polysorbate 80. The most preferred non-ionic surfactant is polysorbate 20.

It is inappropriate to use a non-ionic surfactant at high concentration in liquid formulation, and this is due to the fact that non-ionic surfactant at high concentration induces interference effects when measuring protein concentration and determining protein stability through analytic methods such as UV-spectroscopy or isoelectric focusing, thereby causing difficulty in examining the protein stability accurately. Therefore, the liquid formulation of the present invention comprises the non-ionic surfactant preferably at a low concentration less than 0.2% (w/v), more preferably at 0.001% to 0.02% (w/v).

According to one example of the present invention, when sodium chloride was added as an isotonic agent in the presence of buffer, sugar alcohol, and non-ionic surfactant, the storage stability of long-acting insulin conjugate was significantly increased. In particular, the long-acting insulin conjugate showed remarkably high stability in the formulation comprising 10 mM sodium acetate, 10 to 20 mg/ml sodium chloride, 10% (w/v) mannitol, and 0.02% (w/v) polysorbate 20, having a pH of 6.0. Also, the stability of long-acting insulin conjugate was significantly high in the formulation, comprising 10 mM sodium acetate, 1.2 to 5.9 mg/ml sodium chloride, 2 to 5% (w/v) mannitol, and 0.02% (w/v) polysorbate 20 having a pH of 6.0, for generating equilibrium of osmotic pressure. This indicates that when sodium chloride is used as an isotonic agent together with buffer, sugar alcohol, and non-ionic surfactant, it generates synergic effects, thereby improving the stability of long-acting insulin conjugate.

It is preferred that the stabilizer of the present invention does not contain albumin. Since the human serum albumin available as a stabilizer of protein is produced from human serum, there is always the possibility that it may be contaminated with pathogenic viruses of human origin. Gelatin or bovine serum albumin may cause diseases or may be apt to induce an allergic response in some patients. Free of heterologous proteins such as serum albumins of human or animal origin or purified gelatin, the stabilizer of the present invention has no possibility of causing viral contamination.

In addition, the stabilizer of the present invention may further comprise sugars, polyalcohol, or neutral amino acids. Preferable examples of sugars, which may be further added to increase the storage stability of the long-acting insulin conjugate, include monosaccharides such as mannose, glucose, fucose and xylose, and polysaccharides such as lactose, maltose, sucrose, raffinose and dextran. Preferred examples of polyalcohol include propylene glycol, low-molecular weight polyethylene glycol, glycerol, low-molecular weight polypropylene glycol, and a combination thereof.

Meanwhile, the liquid formulation of long-acting insulin conjugate of the present invention may further comprise a preservative in addition to the above-described conjugate, buffer, isotonic agent, sugar alcohol, and non-ionic surfactant, for the purpose of preventing microbial contamination in multiple-use formulation.

As used herein, "preservative" refers to a compound that is added to a pharmaceutical formulation to act as an antimicrobial. Example of preservative includes benzethonium, chlorohexidine, phenol, m-cresol, benzyl alcohol, methylparaben, propylparaben, chlorobutanol, o-cresol, p-cresol, chlorocresol, benzalconium chloride, phenylmercuric nitrate, thimerosal, and benzoic acid, but is not limited thereto. A single type of preservative may be used individually, or a random combination of two or more types of preservative may be used. Preferably, the liquid formulation of the present invention may comprise one or more of m-cresol, phenol, and benzyl alcohol as a preservative. The liquid formulation of the present invention may comprise 0.001% to 1% (w/v) preservative, and preferably 0.001% to 0.5% (w/v) preservative, and more preferably 0.001 to 0.25% (w/v) preservative.

In one example of the present invention, 0.27% (w/v) m-cresol was added as a preservative in the liquid formulation of the present invention, and the effect of cresol on the stability of insulin conjugate was evaluated. As a result, it was confirmed that the conjugate remained stable in the formulation added with preservative, without precipitation. Therefore, the liquid formulation of insulin conjugate of the present invention, which comprises a preservative in addition to the stabilizer, may be used for multiple administrations.

The liquid formulation of the present invention may further comprise other substances and materials known in the art selectively in addition to the above-described buffer, isotonic agent, sugar alcohol, and non-ionic surfactant, and preservative, as long as the effect of the present invention is not affected.

The albumin-free liquid formulation of long-acting insulin conjugate according to the present invention providing stability to the long-acting insulin conjugate does not have a risk of viral contamination, while providing an excellent storage stability with a simple formulation, and thus the present formulation can be provided more cost-effectively compared to other stabilizer or free-dried formulation.

Also, since the liquid formulation of the present invention comprises the long-acting insulin conjugate which has an enhanced duration of physiological activity compared to a wild-type, it can be used as an effective drug formulation by retaining the protein activity in the body for a longer period compared to the conventional insulin formulation. Also, the present liquid formulation provides an excellent stability for storing a long-acting insulin conjugate at low concentration as well as the one at high concentration.

As another aspect, the present invention provides a method for preparing the liquid formulation of the present invention.

The liquid formulation of the present invention can be prepared by generating long-acting insulin conjugate, and mixing the generated long-acting insulin conjugate with a stabilizer comprising a buffer, sugar alcohol, non-ionic surfactant, and isotonic agent. Also, a stable liquid formulation of long-acting insulin conjugate for multiple uses can be prepared by adding a preservative in addition to the stabilizer.

As another aspect, the present invention provides a composition for preventing or treating diabetes, comprising the insulin conjugate.

The insulin conjugate may be in a liquid formulation, which is the same as described above.

As used herein, "diabetes" refers to a metabolic disease where secretion of insulin is lacking or insulin cannot function properly. By administering the composition of the present invention to a subject, diabetes may be treated by regulating blood glucose level. As used herein, the term "treatment" refers to all actions that can alleviate or beneficially change the symptoms of diabetes by administering the composition of the present invention, and the term "prevention" refers to all actions that suppress or delay the onset of diabetes by administering the composition. The treatment of diabetes that alleviates or beneficially changes the symptoms can be applied to any mammals which may develop diabetes, and examples of such mammals include human and primates, as well livestock such as cows, pigs, sheep, horses, dogs, and cats without limitation, and preferably human.

As used herein, the term "administration" refers to the introduction of predetermined amount of a substance into the patient by a certain suitable method. The compositions may be administered via any of the conventional routes, as long as it is able to reach a target tissue. The routes for administration include intraperitoneal, intravenous, intramuscular, subcutaneous, intradermal, oral, topical, intranasal, intrapulmonary and intrarectal administration, but are not limited thereto. However, since peptides are digested upon oral administration, active ingredients of a composition for oral administration need to be coated or formulated for protection against degradation in the stomach. Preferably, the conjugate may be administered in an injectable form. In addition, the compositions may be administered using a certain apparatus capable of transporting the active ingredients into a target cell.

In addition, the pharmaceutical composition of the present invention can be determined by several factors including the types of diseases to be treated, administration routes, the age, gender, and weight of patient, and severity of disease, as well as the types of active component in drug.

Furthermore, the pharmaceutical composition of the present invention may comprise pharmaceutically acceptable carriers. As used herein, "pharmaceutically acceptable carrier"? refers to a carrier or diluent that does not interrupt the physiological activity and properties of the administered compound without stimulating a subject. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable formulation, the pharmaceutically acceptable carrier may include a buffering agent, a preserving agent, an analgesic, a solubilizer, an isotonic agent, and a stabilizer. For formulations of topical administration, the pharmaceutically acceptable carrier may include a base, an excipient, a lubricant, and a preservative. The pharmaceutical composition of the present invention may be formulated in various forms by adding the pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into single-dose ampule or multidose container. The pharmaceutical composition may be also formulated into solutions, suspensions, tablets, pills, capsules and sustained release formulation.

The liquid formulation of long-acting insulin conjugate of the present invention comprises a therapeutically effective amount of long-acting insulin conjugate. In general, the therapeutically effective amount of Lantus (Insulin glargine; Sanofi Aventis) as an example is about 0.07 mg to 3.7 mg per day. On the other hand, the maximum acceptable dose of insulin of the present invention is as high as about 0.5 mg to 25.9 mg per day, since it only needs to be administered once per several weeks without the need of frequent administration.

As another aspect, the present invention provides a method for preventing or treating diabetes, comprising administering the composition comprising the long-acting insulin conjugate to a subject having diabetes.

The composition of the present invention comprising the long-acting insulin conjugate can effectively reduce the blood glucose level even by a single administration per week without causing the side effect of weight gain, and thus it can be effectively used for preventing or treating diabetes.

Mode for Invention

Hereinafter, the present invention will be described in more detail with reference to Examples. However, these Examples are for illustrative purposes only, and the invention is not intended to be limited by these Examples.

Example 1

Confirmation of the Factors Determining the Stability of the Liquid Formulation of Long-Acting Insulin Conjugate The long-acting insulin conjugate was developed to have an increased half-life in blood without causing low blood glucose level in the body. The insulin conjugate, wherein an immunoglobulin Fc region, non-peptidyl polymer, and insulin are site-specifically conjugated through covalent bonding, has an increased half-life in blood and can remarkably reduce the risk of low blood glucose level.

To confirm the stability of the liquid formulation of the long-acting insulin conjugate, the formulations were prepared in the compositions of Table 1 and stored at 40° C. for 2 weeks, and the stability thereof was analyzed by ion exchange chromatography (IE-HPLC).

At this time, the main factors compared to determine their effects on the stability of conjugate were pH, a type and concentration of buffer, a type of isotonic agent, a concentration of sugar alcohol consisting of mannitol, a type of surfactant, a concentration of surfactant consisting of polysorbate 20, the presence of other additives, and join addition of methionine and sodium chloride.

IE-HPLC (%) results of Table 1 represents the value of "area %/start area %" demonstrating the residual purity of the long-acting insulin conjugate compared to the initial purity.

TABLE 1

| Main Factors | | IE-HPLC (%) |
|---|---|---|
| pH | 5.0~5.4 | Protein precipitation |
| | 5.6 | 87.9 |
| | 6.0 | 88.1 |
| | 6.5 | 81.9 |
| | 7.0 | 70.4 |
| Type of buffer | Sodium acetate | 91.5 |
| | Sodium citrate | 90.5 |
| | Sodium phosphate | 89.4 |
| | Histidine | Protein precipitation |
| Concentration of buffer | 5 mM Sodium acetate | 83.2 |
| | 10 mM Sodium acetate | 83.6 |
| | 20 mM Sodium acetate | 83.5 |
| | 40 mM Sodium acetate | 83.4 |
| Type of isotonic agent | Sodium chloride | 83.5 |
| | Glycerin | 81.7 |
| | Sorbitol | 81.6 |
| Concentrration of mannitol | 2.5% | 74.4 |
| | 5.0% | 76.1 |
| | 10.0% | 76.8 |
| Type of surfactant | Polysorbate 20 | 83.5 |
| | Polysorbate 80 | 83.3 |
| | poloxamer 188 | 83.0 |
| Concentration of polysorbate 20 | 0.005% | 88.4 |
| | 0.01% | 88.5 |
| | 0.02% | 88.9 |
| Presence of other additives | w/o zinc chloride | 77.9 |
| | w/ 20 µg/ml zinc chloride | 70.9 |
| | w/o phenol | 74.4 |
| | w/ 1.5 mg/ml phenol | 73.5 |
| | w/o methionine | 74.4 |
| | w/ 0.1 mg/ml methionine | 77.0 |

TABLE 2

| | pH | Buffer | Isotonic agent | Sugar alcohol | Surfactant |
|---|---|---|---|---|---|
| #1 | 5.6 | 10 mM Sodium acetate | 10 mg/ml NaCl | 10% Mannitol | 0.02% Polysorbate 20 |
| #2 | 6.0 | 10 mM Sodium acetate | 10 mg/ml NaCl | 10% Mannitol | 0.02% Polysorbate 20 |

As results of analysis, the liquid formulation of long-acting insulin conjugate was most stable when it comprised a buffer consisting of sodium acetate, an isotonic agent consisting of sodium chloride, a sugar alcohol consisting of mannitol, a surfactant consisting of polysorbate 20, at a pH of 5.6 or 6.0 as shown in Table 2.

Example 2

Evaluation of the Stability of Long-Acting Insulin Conjugate Depending on the Concentrations of Isotonic Agent and Surfactant Based on the liquid formulation confirmed in Example 1 (10 mM sodium acetate at pH 6.0, 10 mg/ml sodium chloride, 10% (w/v) mannitol, 0.02% (w/v) polysorbate 20), the stability of the long-acting insulin conjugate was examined depending on the concentrations of isotonic agent and surfactant. At this time, the concentrations of isotonic agent and surfactant were set to be within the maximum acceptable range recommended by commercially available formulations and permitting institution.

The liquid formulations of long-acting insulin conjugate were prepared in the compositions of Table 3 and stored at 40° C. for 4 weeks. Then the stability was examined by IE-HPLC and size exclusion chromatography (SE-HPLC).

IE-HPLC (%) and SE-HPLC (%) results of Table 4 represent the value of "area %/start area %" demonstrating the residual purity of long-acting insulin conjugate compared to the initial purity.

TABLE 3

|  | pH | Buffer | Isotonic agent | Sugar alcohol | Surfactant |
|---|---|---|---|---|---|
| Control group | 6.0 | 10 mM Sodium acetate | 10 mg/ml NaCl | 10% Mannitol | 0.02% Polysorbate 20 |
| #1 | 6.0 | 10 mM Sodium acetate | 10 mg/ml NaCl | 10% Mannitol | 0.2% Polysorbate 20 |
| #2 | 6.0 | 10 mM Sodium acetate | 20 mg/ml NaCl | 10% Mannitol | 0.02% Polysorbate 20 |

TABLE 4

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control group | 100 | 90.47 | 81.82 | 73.64 | 64.92 | 100 | 97.26 | 95.66 | 92.38 | 90.16 |
| #1 | 100 | 90.29 | 81.97 | 73.38 | N/A* | 100 | 97.19 | 95.54 | 92.18 | N/A |
| #2 | 100 | 91.44 | 83.66 | 75.62 | 66.76 | 100 | 97.79 | 96.46 | 93.87 | 92.02 |

N/A: data not available due to precipitation by aggregation

As shown above, when the concentration of sodium chloride was increased to 20 mg/ml (Test group #2) in the liquid formulation confirmed in Example 2 (10 mM sodium acetate, pH 6.0, mg/ml sodium chloride, 10% (w/v) mannitol, 0.02% (w/v) polysorbate 20), the stability of the conjugate was the greatest. On the other hand, when the concentration of polysorbate 20 was increased to 0.2% (w/v) (Test group #1), protein precipitation occurred 3 weeks after storing the formulation, and after 4 weeks of storage, the precipitation level was increased (Table 4).

Example 3

Evaluation of the Stability of Long-Acting Insulin Conjugate Depending on the Type of Sugar Alcohol Examples of the sugar alcohol that can be added to the formulation to enhance the storage stability of long-acting insulin conjugate include monosaccharides such as mannose, glucose, fucose, and xylose; and polysaccharides such as lactose, maltose, sucrose, raffinose, and dextran. Among them, sucrose was tested for its effect on the stability of long-acting insulin conjugate, since sucrose was confirmed to have the effect of reducing deamidation (J. of Pharmaceutical Sciences, Vol. 94, 2005). At this time, the concentration of sucrose was within the maximum acceptable range recommended by commercially available formulations and permitting institution.

The liquid formulations of long-acting insulin conjugate were prepared in the compositions of Table 5 and stored at 40° C. for 4 weeks, and the stability thereof was examined by performing stability test using IE-HPLC and SE-HPLC. IE-HPLC (%) and SE-HPLC (%) of Table 6 represent the value of "area %/start area %" demonstrating the residual purity of long-acting insulin conjugate compared to the initial purity.

TABLE 5

|  | pH | Buffer | Isotonic Agent | Sugar Alcohol | Surfactant |
|---|---|---|---|---|---|
| Control Group | 6.0 | 10 mM Sodium acetate | 10 mg/ml NaCl | 10% Mannitol | 0.02% Polysorbate 20 |
| #1 | 6.0 | 10 mM Sodium acetate | 10 mg/ml NaCl | 7% Sucrose | 0.02% Polysorbate 20 |
| #2 | 6.0 | 10 mM Sodium acetate | 10 mg/ml NaCl | 7% Sucrose | 0.2% Polysorbate 20 |
| #3 | 6.0 | 10 mM Sodium acetate | 20 mg/ml NaCl | 7% Sucrose | 0.02% Polysorbate 20 |

TABLE 6

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control group | 100 | 90.47 | 81.82 | 73.64 | 64.92 | 100 | 97.26 | 95.66 | 92.38 | 90.16 |
| #1 | 100 | 89.46 | 82.06 | 73.28 | 63.08 | 100 | 97.21 | 95.63 | 92.47 | 90.28 |
| #2 | 100 | 90.43 | 82.00 | 73.42 | 61.25 | 100 | 96.96 | 95.62 | 92.43 | 90.21 |
| #3 | 100 | 90.45 | 81.96 | 73.84 | 64.90 | 100 | 97.27 | 95.77 | 92.85 | 90.52 |

As shown above, when sucrose was added instead of mannitol as a sugar alcohol that can be added to enhance the storage stability of long-acting insulin conjugate (Test Group #1), the stability of formulation was similar to that of control group of liquid formulation (10 mM sodium acetate, pH 6.0, 10 mg/ml sodium chloride, 10% (w/v) mannitol, 0.02% (w/v) Polysorbate 20). Also, when the concentration of sodium chloride was increased to 20 mg/ml in the liquid formulation comprising sucrose (Test group #3), the stability of the liquid formulation was similar to that of control group of liquid formulation. Furthermore, when the concentration of polysorbate 20 was increased to 0.2% (w/v) (Test group #2), the stability of the liquid formulation was reduced compared to the group without the increase of polysorbate 20 concentration, and it also caused protein precipitation after 3 weeks of storage. As for Test group #2, the purity was examined after removing precipitates, and it was confirmed that the stability of Test group #2 was reduced compared to other formulations (Table 6).

Example 4

Evaluation of Stability of Long-Acting Insulin Conjugate at Various pH

Based on the liquid formulation consisting of buffer, sodium chloride, mannitol, and polysorbate 20, the stability of long-acting insulin conjugate was examined at various pH.

The liquid formulations of long-acting insulin conjugate were prepared in the composition of Table 7, and stored at 40° C. for 4 weeks. Then the stability of the formulations was examined by monitoring protein precipitation with naked eyes.

TABLE 7

|  | pH | Buffer | Isotonic agent | Sugar alcohol | Surfactant |
|---|---|---|---|---|---|
| Control group | 6.0 | 10 mM Sodium acetate | 10 mg/ml NaCl | 10% Mannitol | 0.02% Polysorbate 20 |
| #1 | 5.2 | 10 mM Sodium acetate | 10 mg/ml NaCl | 10% Mannitol | 0.2% Polysorbate 20 |
| #2 | 5.6 | 10 mM Sodium acetate | 10 mg/ml NaCl | 10% Mannitol | 0.2% Polysorbate 20 |
| #3 | 6.0 | 10 mM Sodium acetate | 10 mg/ml NaCl | 10% Mannitol | 0.2% Polysorbate 20 |

TABLE 7-continued

|  | pH | Buffer | Isotonic agent | Sugar alcohol | Surfactant |
|---|---|---|---|---|---|
| #4 | 5.2 | 10 mM Sodium acetate | 20 mg/ml NaCl | 10% Mannitol | 0.02% Polysorbate 20 |
| #5 | 5.6 | 10 mM Sodium acetate | 20 mg/ml NaCl | 10% Mannitol | 0.02% Polysorbate 20 |
| #6 | 6.0 | 10 mM Sodium acetate | 20 mg/ml NaCl | 10% Mannitol | 0.02% Polysorbate 20 |
| #7 | 5.2 | 10 mM Sodium. acetate | 20 mg/ml NaCl | 10% Mannitol | 0.2% Polysorbate 20 |
| #8 | 5.6 | 10 mM Sodium acetate | 20 mg/ml NaCl | 10% Mannitol | 0.2% Polysorbate 20 |
| #9 | 6.0 | 10 mM Sodium acetate | 20 mg/ml NaCl | 10% Mannitol | 0.2% Polysorbate 20 |

The duration of absence of protein precipitation (in week) in FIG. 1 represents the time during which protein precipitation did not occur after storing the formulation at 40° C. As shown above, in 10 mM sodium acetate, pH 5.2 (Test groups #1, #4, and #7), protein precipitation occurred at 40° C. within 1 week of storage. In 10 mM sodium acetate, pH 5.6 (Test groups #2, #5, and #8), protein precipitation occurred at 40° C. within 2 weeks of storage. However, when in 10 mM sodium acetate, pH 6.0 (Test groups #3, #6, and #9), protein precipitation did not occur at 40° C. for up to 3 weeks. Among these, when the concentration of sodium chloride was increased to 20 mg/ml in 10 mM sodium acetate, pH 6.0 (Test group #6), the stability of the conjugate was the greatest (FIG. 1).

Example 5

Evaluation of the Stability of Long-Acting Insulin Conjugate Depending on the High Concentrations of Isotonic Agent and Surfactant Individually or in Combination Having the liquid formulation confirmed in Examples 1 to 4 (10 mM sodium acetate, pH 6.0, 10 mg/ml sodium chloride, 10% (w/v) mannitol, 0.02% (w/v) polysorbate 20) as a basis, 20 mg/ml sodium chloride as isotonic agent at high concentration and 0.2% (w/v) polysorbate 20 as surfactant at high concentration were added individually or concurrently. Then the stability of formulations was compared.

The liquid formulations of long-acting insulin conjugate were prepared in the composition of Table 8 and stored at 40° C. for 4 weeks. Then the stability thereof was examined by performing a stability test using IE-HPLC and SE-HPLC.

IE-HPLC (%) and SE-HPLC (%) of Table 9 represent the value of "area %/start area %" demonstrating the residual purity of long-acting insulin conjugate compared to the initial purity.

TABLE 8

|  | pH | Buffer | Isotonic agent | Sugar alcohol | Surfactant |
|---|---|---|---|---|---|
| Control group | 6.0 | 10 mM Sodium acetate | 10 mg/ml NaCl | 10% Mannitol | 0.02% Polysorbate 20 |
| #1 | 6.0 | 10 mM Sodium acetate | 10 mg/ml NaCl | 10% Mannitol | 0.2% Polysorbate 20 |
| #2 | 6.0 | 10 mM Sodium acetate | 20 mg/ml NaCl | 10% Mannitol | 0.02% Polysorbate 20 |
| #3 | 6.0 | 10 mM Sodium acetate | 20 mg/ml NaCl | 10% Mannitol | 0.2% Polysorbate 20 |

TABLE 9

|  | IE-HPLC (%) | | | | | SE-HPLC (%) | | | | |
|---|---|---|---|---|---|---|---|---|---|---|
|  | Start | 1 week | 2 weeks | 3 weeks | 4 weeks | start | 1 week | 2 weeks | 3 weeks | 4 weeks |
| Control group | 100 | 90.47 | 81.82 | 73.64 | 64.92 | 100 | 97.26 | 95.66 | 92.38 | 90.16 |
| #1 | 100 | 90.29 | 81.97 | 73.38 | N/A | 100 | 97.19 | 95.54 | 92.18 | N/A |
| #2 | 100 | 91.44 | 83.66 | 75.62 | 66.76 | 100 | 97.79 | 96.46 | 93.87 | 92.02 |
| #3 | 100 | 91.37 | N/A | N/A | N/A | 100 | 97.83 | N/A | N/A | N/A |

Figure 2A:
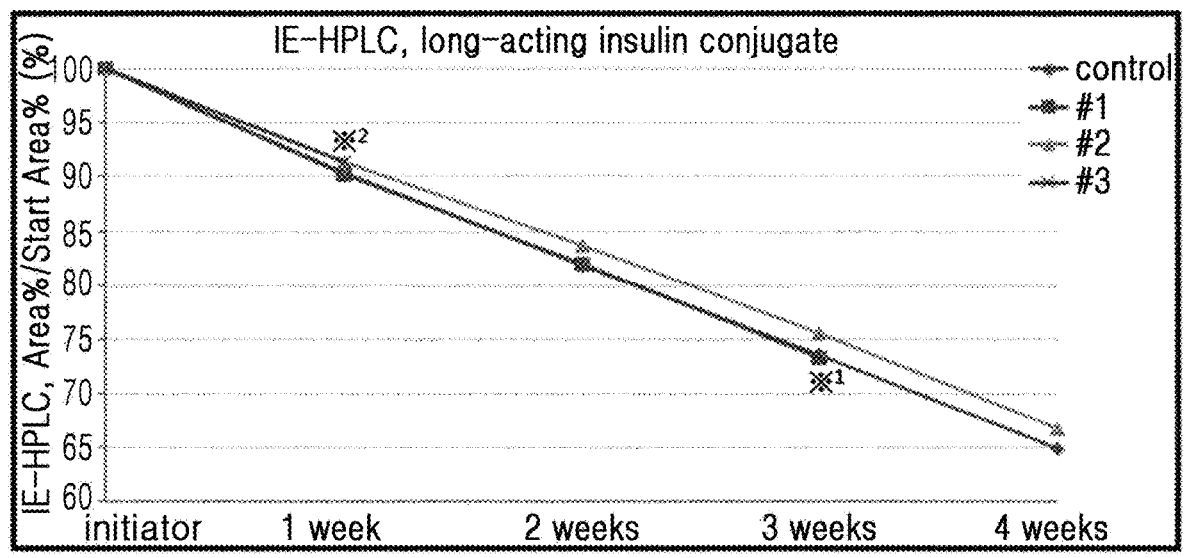
FIG. 2A shows the a graph of instability severity test by ion exchange chromatography (IE-HPLC) and FIG. 2B shows a graph of instability severity test by size exclusion chromatography (SE-HPLC) each on the liquid formulation of long-acting insulin conjugate at 40° C. The control group was the liquid formulation confirmed in Examples 1 to 4 (10 mM sodium acetate at pH 6.0, 10 mg/ml sodium chloride, 10% (w/v) mannitol, 0.02% (w/v) polysorbate 20). Based on this, the first test group (line #1) was prepared by adding 0.2% (w/v) polysorbate 20 as a surfactant at high concentration to the liquid formulation, the second test group (line #2) was prepared by adding 20 mg/ml sodium chloride as an isotonic agent at high concentration, and the third test group (line #3) was prepared by adding both of 0.2% (w/v) polysorbate 20 and 20 mg/ml sodium chloride. As a result, the test group #2 of liquid formulation comprising sodium acetate at a pH of 6.0, sodium chloride, mannitol, and polysorbate 20, wherein the concentration of sodium chloride was increased to 20 mg/ml, maintained higher stability than the control group (10 mg/ml sodium chloride). However, when the concentration of polysorbate 20 was increased to 0.2% (w/v) (test group #1), the protein precipitation occurred 3 weeks after storing the formulation. When the concentrations of sodium chloride and polysorbate 20 were both increased to 20 mg/ml and 0.2% (w/v) respectively, the liquid formulation (#3) showed protein precipitation 1 week after storing the formulation.
Figure 2B:
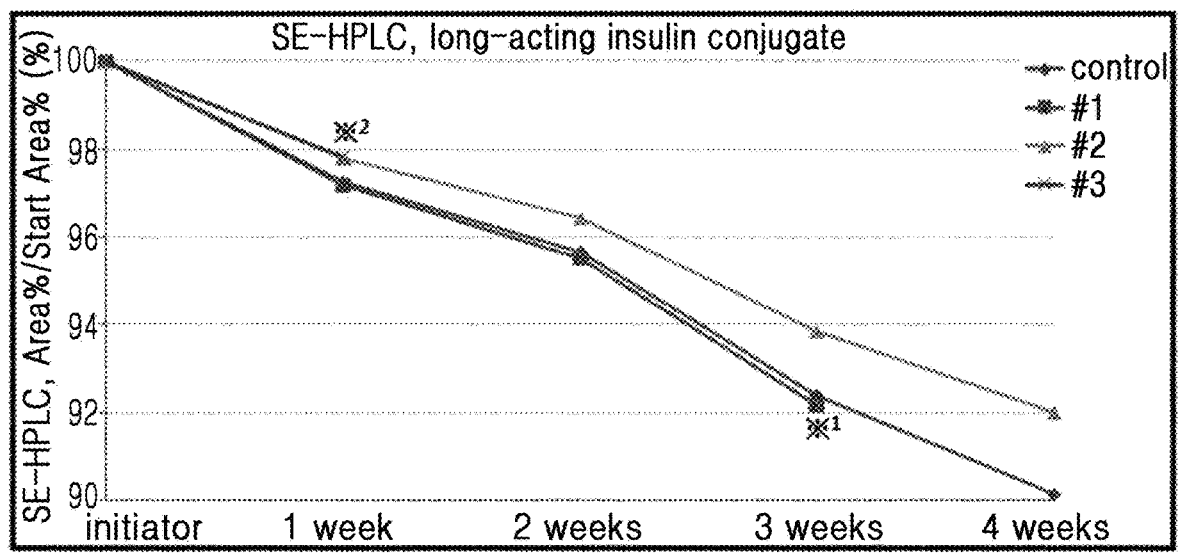

As shown above, when the concentration of sodium chloride was increased to 20 mg/ml (Test group #2) compared to the control group of liquid formulation (10 mM sodium acetate, pH 6.0, 10 mg/ml sodium chloride, 10% (w/v) mannitol, 0.02% (w/v) polysorbate 20), the stability of the conjugate was the greatest. On the other hand, when the concentration of polysorbate 20 was increased to 0.2% (w/v) (Test group #1), protein precipitation occurred after 3 weeks of storage, which was increased after 4 weeks of storage. Also, when 20 mg/ml sodium chloride as isotonic agent at high concentration and 0.2% (w/v) polysorbate 20 as surfactant at high concentration were added simultaneously (Test group #3), protein precipitation occurred at 40° C. within 2 weeks of storage (Table 9, FIG. 2A (IE-HPLC), and FIG. 2B (SE-HPLC)).

Example 6

Evaluation of the Stability of Long-Acting Insulin Conjugate Depending on the Addition of Isotonic Agent at Low Concentration and Sugar Alcohol at Low Concentration Having the liquid formulation confirmed in Examples 1 to 4 (10 mM sodium acetate, pH 6.0, 10 mg/ml sodium chloride, 10% (w/v) mannitol, 0.02% (w/v) polysorbate 20) as a basis, the liquid formulations having a combination of 1.2 to 5.9 mg/ml sodium chloride as isotonic agent at low concentration and 2 to 5% (w/v) mannitol as sugar alcohol at low concentration was prepared, and the stability of the long-acting insulin conjugate therein was examined.

The liquid formulations of long-acting insulin conjugate were prepared in the composition of Table 10 and stored at 25° C. for 4 weeks. Then the stability of the conjugate was examined by performing a stability test using IE-HPLC and SE-HPLC.

IE-HPLC (%) and SE-HPLC (%) of Table 11 represent the value of "area %/start area %" demonstrating the residual purity of long-acting insulin conjugate compared to the initial purity.

TABLE 10

|  | pH | Buffer | Isotonic agent | Sugar alcohol | Surfactant |
|---|---|---|---|---|---|
| Control group | 6.0 | 10 mM Sodium acetate | 10 mg/ml NaCl | 10% Mannitol | 0.02% Polysorbate 20 |

TABLE 10-continued

|  | pH | Buffer | Isotonic agent | Sugar alcohol | Surfactant |
|---|---|---|---|---|---|
| #1 | 6.0 | 10 mM Sodium acetate | 5.9 mg/ml NaCl | 2% Mannitol | 0.02% Polysorbate 20 |
| #2 | 6.0 | 10 mM Sodium acetate | 1.2 mg/ml NaCl | 5% Mannitol | 0.2% Polysorbate 20 |

TABLE 11

| | IE-HPLC (%) | | | | | SE-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control group | 100 | 99.75 | 98.86 | 97.49 | 95.79 | 100 | 99.80 | 99.53 | 99.31 | 99.15 |
| #1 | 100 | 99.72 | 98.87 | 97.50 | 95.78 | 100 | 99.80 | 99.55 | 99.33 | 99.14 |
| #2 | 100 | 99.72 | 98.85 | 97.53 | 95.72 | 100 | 99.78 | 99.54 | 99.32 | 98.99 |

As shown above, the liquid formulations comprising 1.2 to 5.9 mg/ml sodium chloride as isotonic agent and 2 to 5% (w/v) mannitol as sugar alcohol (Test group #1, #2) showed comparable stability with the liquid formulation confirmed in Examples 1 to 4 (10 mM sodium acetate, pH 6.0, 10 mg/ml sodium chloride, 10% (w/v) mannitol, 0.02% (w/v) polysorbate 20).

Example 7

Evaluation of the Stability of Long-Acting Insulin Conjugate Depending on the Addition of Preservative The stability of long-acting insulin conjugate was compared when the preservative is added to the liquid formulation confirmed in Examples 1 to 4 (10 mM sodium acetate, pH 6.0, 10 mg/ml sodium chloride, 10% (w/v) mannitol, 0.02% (w/v) polysorbate 20) and to the liquid formulation confirmed in Example 6 (10 mM sodium acetate, pH 6.0, 1.2 to 5.9 mg/ml sodium chloride, 2 to 5% (w/v) mannitol, 0.02% (w/v) polysorbate 20) for generating equilibrium of osmotic pressure.

The liquid formulation of long-acting insulin conjugate was prepared in the composition of Table 12 and stored at 25° C. for 4 weeks. Then the stability of the conjugate was examined by performing a stability test using IE-HPLC and SE-HPLC.

IE-HPLC (%) and SE-HPLC (%) of Table 13 represent "area %/start area %" demonstrating the residual purity of long-acting insulin conjugate compared to the initial purity.

TABLE 12

|  | pH | Buffer | Isotonic agent | Sugar alcohol | Surfactant | Preservative |
|---|---|---|---|---|---|---|
| Control group | 6.0 | 10 mM Sodium acetate | 10 mg/ml NaCl | 10% Mannitol | 0.02% Polysorbate 20 | — |
| #1 | 6.0 | 10 mM Sodium acetate | 10 mg/ml NaCl | 10% Mannitol | 0.02% Polysorbate 20 | 0.27% m-cresol |
| #2 | 6.0 | 10 mM Sodium acetate | 5.9 mg/ml NaCl | 2% Mannitol | 0.02% Polysorbate 20 | — |
| #3 | 6.0 | 10 mM Sodium acetate | 5.9 mg/ml NaCl | 2% Mannitol | 0.02% Polysorbate 20 | 0.27% m-cresol |
| #4 | 6.0 | 10 mM Sodium acetate | 1.2 mg/ml NaCl | 5% Mannitol | 0.02% Polysorbate 20 | — |
| #5 | 6.0 | 10 mM Sodium acetate | 1.2 mg/ml NaCl | 5% Mannitol | 0.02% Polysorbate 20 | 0.27% m-cresol |

TABLE 13

|  | IE-HPLC (%) | | | | | SE-HPLC (%) | | | | |
|---|---|---|---|---|---|---|---|---|---|---|
|  | Start | 1 week | 2 weeks | 3 weeks | 4 weeks | Start | 1 week | 2 weeks | 3 weeks | 4 weeks |
| Control group | 100 | 99.75 | 98.86 | 97.49 | 95.79 | 100 | 99.80 | 99.53 | 99.31 | 99.15 |
| #1 | 100 | 99.67 | 98.55 | 96.66 | 94.54 | 100 | 99.64 | 99.30 | 98.62 | 98.31 |
| #2 | 100 | 99.72 | 98.87 | 97.50 | 95.78 | 100 | 99.80 | 99.55 | 99.33 | 99.14 |
| #3 | 100 | 99.65 | 98.68 | 96.64 | 94.61 | 100 | 99.62 | 99.32 | 98.63 | 98.33 |
| #4 | 100 | 99.72 | 98.85 | 97.53 | 95.72 | 100 | 99.78 | 99.54 | 99.32 | 98.99 |
| #5 | 100 | 99.63 | 98.63 | 96.59 | 94.53 | 100 | 99.59 | 99.18 | 98.49 | 98.01 |

As shown above, the liquid formulations comprising 0.27% (w/v) m-cresol as a preservative (Test groups #1, #3, and #5) showed comparable stability with the liquid formulations without the preservative (control group, #2, and #4), as shown by adding 0.27% (w/v) m-cresol to the liquid formulation confirmed in Examples 1 to 4 (10 mM sodium acetate, pH 6.0, 10 mg/ml sodium chloride, 10% (w/v) mannitol, 0.02% (w/v) polysorbate 20) and to the liquid formulation confirmed in Example 6 for the same osmotic pressure (10 mM sodium acetate, pH 6.0, 1.2 to 5.9 mg/ml sodium chloride, 2 to 5% (w/v) mannitol, 0.02% (w/v) polysorbate 20).

These results demonstrate that the composition of the present liquid formulation of the present invention could maintain a high stability of long-acting insulin conjugate, even when a preservative is further added to the composition.

Based on the above description, it will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A pharmaceutical liquid formulation of long-acting insulin conjugate, consisting of
a pharmaceutically effective amount of a long-acting insulin conjugate, wherein an insulin which is a physiologically active peptide, is linked to an immunoglobulin Fc region;
5 mM to 50 mM of an acetate buffer having a pH of a range from 5.6 to 6.5;
2% to 10% (w/v) of a sugar alcohol
0.005% to 0.02% (w/v) of a polysorbate 20;
1.2 to 20 mg/ml of an isotonic agent; and
optionally a preservative.

2. The pharmaceutical liquid formulation of long-acting insulin conjugate according to claim 1, wherein the insulin has the same amino acid sequence as native insulin.

3. The pharmaceutical liquid formulation of long-acting insulin conjugate according to claim 1, wherein the insulin is an insulin derivative which is generated by amino acid substitution, deletion, or insertion of native insulin or a peptide analogue which shows similar activity as native insulin.

4. The pharmaceutical liquid formulation of long-acting insulin conjugate according to claim 1, wherein the immunoglobulin Fc region is a Fc region derived from IgG, IgA, IgD, IgE, or IgM.

5. The pharmaceutical liquid formulation of long-acting insulin conjugate according to claim 4, wherein the immunoglobulin Fc region is a hybrid of domains of different origins derived from immunoglobulins selected from the group consisting of IgG, IgA, IgD, IgE, and IgM.

6. The pharmaceutical liquid formulation of long-acting insulin conjugate according to claim 4, wherein the immunoglobulin Fc region is a dimer or multimer consisting of single-chain immunoglobulins composed of domains of same origin.

7. The pharmaceutical liquid formulation of long-acting insulin conjugate according to claim 6, wherein the immunoglobulin Fc region is a human aglycosylated IgG4 Fc region.

8. The pharmaceutical liquid formulation of long-acting insulin conjugate according to claim 1, wherein the conjugate is linked by using a non-peptidyl polymer or a recombination technique.

9. The pharmaceutical liquid formulation of long-acting insulin conjugate according to claim 8, wherein the non-peptidyl polymer is a polyethylene glycol.

10. The pharmaceutical liquid formulation of long-acting insulin conjugate according to claim 8, wherein the non-peptidyl polymer is selected from the group consisting of a polypropylene glycol, a copolymer of ethylene glycol and propylene glycol, a polyoxyethylated polyol, polyvinyl alcohol, polysaccharide, dextran, polyvinyl ethyl ether, polylactic acid, and polylactic-glycolic acid, a lipid polymer, a chitin, a hyaluronic acid, and a combination thereof.

11. The pharmaceutical liquid formulation of long-acting insulin conjugate according to claim 1, wherein the pharmaceutically effective amount of long-acting insulin conjugate is 10 mg/ml to 200 mg/ml based on a total volume of the liquid formulation.

12. The pharmaceutical liquid formulation of long-acting insulin conjugate according to claim 1, wherein the sugar alcohol is one or more selected from the group consisting of mannitol, sucrose, and sorbitol.

13. The pharmaceutical liquid formulation of long-acting insulin conjugate according to claim 1, wherein the isotonic agent is selected from the group consisting of sodium chloride, sodium sulfate, and sodium citrate.

14. The pharmaceutical liquid formulation of long-acting insulin conjugate according to claim 1, wherein the isotonic agent is sodium chloride.

15. A pharmaceutical liquid formulation of long-acting insulin conjugate, consisting of a pharmaceutically effective amount of a long-acting insulin conjugate, wherein an insulin which is a physiologically active peptide, is linked to an immunoglobulin Fc region;
5 mM to 50 mM of an acetate buffer having a pH of a range from 5.6 to 6.5,
2% to 10% (w/v) of a sugar alcohol,
0.005% to 0.02% (w/v) of a polysorbate 20,
1.2 to 20 mg/ml of an isotonic agent, and
0 to 0.1 mg/ml of an amino acid.

16. The pharmaceutical liquid formulation of long-acting insulin conjugate of claim 1, wherein the insulin and the immunoglobulin Fc region are linked by polyethylene glycol,
wherein the sugar alcohol is mannitol; and
wherein the isotonic agent is sodium chloride.

17. The pharmaceutical liquid formulation of long-acting insulin conjugate according to claim 16, wherein the acetate buffer is a 10 mM sodium acetate buffer; wherein the mannitol, sodium chloride, and polysorbate 20 are contained in an amount of 10% (w/v), 10-20 mg/ml, and 0.02% (w/v), respectively, based on the pharmaceutical liquid formulation; and wherein the pharmaceutical liquid formulation has a pH of 6.0.

18. The pharmaceutical liquid formulation of long-acting insulin conjugate according to claim 16, wherein the acetate buffer is a 10 mM sodium acetate buffer wherein the mannitol, sodium chloride, and polysorbate 20 are contained in an amount of 2% to 5% (w/v), 1.2 to 6 mg/ml, and 0.02% (w/v), respectively, based on the pharmaceutical liquid formulation; and wherein the pharmaceutical liquid formulation has a pH of 6.0.

19. A pharmaceutical liquid formulation of long-acting insulin conjugate, consisting of
a pharmaceutically effective amount of a long-acting insulin conjugate, wherein an insulin which is a physiologically active peptide, is linked to an immunoglobulin Fc region;
5 mM to 50 mM of an acetate buffer having a pH of a range from 5.6 to 6.5,
2% to 10% (w/v) of a sugar alcohol,
0.005% to 0.02% (w/v) of a polysorbate 20,
1.2 to 20 mg/ml of an isotonic agent and
0.001% to 1% (w/v) of one or more preservatives selected from the group consisting of m-cresol, phenol, and benzyl alcohol.

20. The pharmaceutical liquid formulation of long-acting insulin conjugate according to claim 19, wherein the preservative is m-cresol.

21. The pharmaceutical liquid formulation of long-acting insulin conjugate according to claim 19, which is for multiple administrations.

22. A method for preparing the pharmaceutical liquid formulation of long-acting insulin conjugate of claim 1, comprising (a) preparing a long-acting insulin conjugate; and (b) mixing the long-acting insulin conjugate prepared in step (a) with a stabilizer consisting of 5 mM to 50 mM of a buffer, 2% to 10% (w/v) of a sugar alcohol, 0.005% to 0.02% (w/v) of a non-ionic surfactant, 1.2 to 20 mg/ml of sodium chloride as an isotonic agent, and optionally a preservative;
wherein the buffer is an acetate buffer and has a range of pH 5.6 to 6.5; and
wherein the non-ionic surfactant is polysorbate 20.

23. A method for preparing the pharmaceutical liquid formulation of long-acting insulin conjugate of claim 19, comprising (a) preparing a long-acting insulin conjugate; and (b) mixing the long-acting insulin conjugate prepared in step (a) with a stabilizer consisting of 5 mM to 50 mM of a buffer, 2% to 10% (w/v) of a sugar alcohol, 0.005% to 0.02% (w/v) of a non-ionic surfactant, 1.2 to 20 mg/ml of sodium chloride as an isotonic agent, and 0.001% to 1% (w/v) of a preservative,
wherein the buffer is an acetate buffer and has a range of pH 5.6 to 6.5; and
wherein the non-ionic surfactant is polysorbate 20; and
wherein the preservative is one or more selected from the group consisting of m-cresol, phenol, and benzyl alcohol.

24. The pharmaceutical liquid formulation of long-acting insulin conjugate according to claim 1, wherein the acetate buffer is a 5 mM to 40 mM sodium acetate buffer; wherein the mannitol, sodium chloride as the isotonic agent, and the polysorbate 20 are contained in an amount of 2.5% to 10% (w/v), 10 to 20 mg/ml, and 0.005% to 0.02% (w/v), respectively, based on the pharmaceutical liquid formulation.

25. The pharmaceutical liquid formulation of long-acting insulin conjugate according to claim 19, wherein the stabilizer consists of acetate buffer is a 5 mM to 40 mM sodium acetate buffer; wherein the mannitol, 10 to 20 sodium chloride as the isotonic agent, and the polysorbate 20, and the preservative are contained in an amount of 2.5% to 10% (w/v), 10 to 20 mg/ml, 0.005% to 0.02% (w/v), and 0.001% to 1% (w/v), respectively, based on the pharmaceutical liquid formulation.

26. A pharmaceutical liquid formulation of long-acting insulin conjugate, comprising a pharmaceutically effective amount of a long-acting insulin conjugate, wherein an insulin which is a physiologically active peptide, is linked to an immunoglobulin Fc region; and an albumin-free stabilizer,
wherein the albumin-free stabilizer consists of
5 mM to 50 mM of an acetate buffer,
2% to 10% (w/v) of a sugar alcohol,
0.005% to 0.02% (w/v) of a non-ionic surfactant selected from the group consisting of polysorbate 20, polysorbate 80 and polysorbate 188,
1.2 to 20 mg/ml of sodium chloride, and
one or more additives selected from the group consisting of 0 to 20 µg/ml of zinc chloride, 0 to 1.5 mg/ml of phenol, 0 to 0.1 mg/ml of methionine, and 0 to 1% (w/v) of one or more preservatives selected from the group consisting of m-cresol, phenol, and benzyl alcohol; and
wherein the acetate buffer has a pH ranging from 5.6 to 6.5.

* * * * *